(12) United States Patent
Brunswick

(10) Patent No.: US 9,211,080 B2
(45) Date of Patent: Dec. 15, 2015

(54) METHOD FOR PERFORMING A PHYSIOLOGICAL ANALYSIS WITH INCREASED RELIABILITY

(71) Applicant: IMPETO MEDICAL, Paris (FR)

(72) Inventor: Philippe Brunswick, Paris (FR)

(73) Assignee: IMPETO MEDICAL, Paris (FR)

(*) Notice: Subject to any disclaimer, the term of this patent is extended or adjusted under 35 U.S.C. 154(b) by 0 days.

(21) Appl. No.: 14/359,503

(22) PCT Filed: Nov. 12, 2012

(86) PCT No.: PCT/EP2012/072388
§ 371 (c)(1),
(2) Date: May 20, 2014

(87) PCT Pub. No.: WO2013/075963
PCT Pub. Date: May 30, 2013

(65) Prior Publication Data
US 2014/0330096 A1    Nov. 6, 2014

(30) Foreign Application Priority Data
Nov. 21, 2011 (FR) .................................. 11 60601

(51) Int. Cl.
*A61B 5/00* (2006.01)
*A61B 5/053* (2006.01)

(52) U.S. Cl.
CPC ............ *A61B 5/0531* (2013.01); *A61B 5/4266* (2013.01); *A61B 5/6814* (2013.01); *A61B 5/6825* (2013.01); *A61B 5/6829* (2013.01); *A61B 5/72* (2013.01)

(58) Field of Classification Search
USPC .................................. 600/307, 383, 384, 547
See application file for complete search history.

(56) References Cited

U.S. PATENT DOCUMENTS 3,449,080 A    6/1969   Edwards et al.
3,821,949 A    7/1974   Hartzell et al.
(Continued)

FOREIGN PATENT DOCUMENTS

WO    WO-00/19894 A1      4/2000
WO    WO-2004/043247 A1   5/2004
WO    WO-2006136598 A2   12/2006

OTHER PUBLICATIONS

Ayoub, Hanna, et al. "Electrochemical characterization of nickel electrodes in phosphate and carbonate electrolytes in view of assessing a medical diagnostic device for the detection of early diabetes." Electroanalysis 22.21 (2010): 2483-2490.*

(Continued)

*Primary Examiner* — Michael Kahelin
*Assistant Examiner* — Mitchell E Alter
(74) *Attorney, Agent, or Firm* — Harness, Dickey & Pierce, P.L.C.

(57) ABSTRACT

A method for performing an electrophysiological analysis implemented in a system includes: a series of electrodes to be placed on different regions of the human body; a DC voltage source controlled so as to produce DC voltage pulses; a switching circuit for selectively connecting the active electrodes to the voltage source, the active electrodes forming an anode and a cathode, and for connecting at least one other high-impedance passive electrode used to measure the potential reached by the body; and a measuring circuit for reading data representative of the current in the active electrodes, and data representative of the potentials generated on at least certain high-impedance electrodes in response to the application of the pulses, the data allowing a value to be determined for the electrochemical conductance of the skin. The method also regenerates a high-impedance electrode connected to the voltage source as a cathode.

26 Claims, 4 Drawing Sheets

(56) References Cited

U.S. PATENT DOCUMENTS

| | | |
|---|---|---|
| 4,365,637 A | 12/1982 | Johnson |
| 4,509,531 A | 4/1985 | Ward |
| 4,690,152 A | 9/1987 | Juncosa |
| 4,794,934 A | 1/1989 | Motoyama et al. |
| 5,307,817 A | 5/1994 | Guggenbuhl et al. |
| 5,406,956 A | 4/1995 | Farwell |
| 5,427,113 A | 6/1995 | Hiroshi et al. |
| 5,771,261 A | 6/1998 | Anbar |
| 5,782,884 A | 7/1998 | Stotts et al. |
| 5,800,350 A | 9/1998 | Coppleson et al. |
| 5,928,155 A | 7/1999 | Eggers et al. |
| 5,947,910 A | 9/1999 | Zimmet |
| 6,058,325 A | 5/2000 | Baura |
| 6,175,752 B1 | 1/2001 | Say et al. |
| 6,299,583 B1 | 10/2001 | Eggers et al. |
| 6,336,045 B1 | 1/2002 | Brooks |
| 6,473,641 B1 | 10/2002 | Kodama et al. |
| 6,491,647 B1 | 12/2002 | Bridger et al. |
| 6,512,949 B1 | 1/2003 | Combs et al. |
| 6,517,482 B1 | 2/2003 | Elden et al. |
| 6,571,124 B1 | 5/2003 | Storm |
| 6,577,893 B1 | 6/2003 | Besson et al. |
| 6,871,084 B1 | 3/2005 | Kingsley et al. |
| 7,161,362 B2 | 1/2007 | Shambroom et al. |
| 7,477,937 B2 | 1/2009 | Iijima et al. |
| 7,931,592 B2 | 4/2011 | Currie et al. |
| 8,085,144 B2 | 12/2011 | Appelt et al. |
| 8,655,443 B2 | 2/2014 | Brunswick et al. |
| 8,918,170 B2 | 12/2014 | Brunswick et al. |
| 8,934,954 B2 | 1/2015 | Brunswick et al. |
| 8,965,497 B2 | 2/2015 | Tournefier et al. |
| 2002/0107452 A1 | 8/2002 | Kwong |
| 2003/0078505 A1 | 4/2003 | Kim et al. |
| 2003/0135094 A1 | 7/2003 | Illyes et al. |
| 2004/0128088 A1 | 7/2004 | Laletin et al. |
| 2005/0069925 A1 | 3/2005 | Ford et al. |
| 2005/0101876 A1 | 5/2005 | Pearlman |
| 2005/0113650 A1 | 5/2005 | Pacione et al. |
| 2005/0178185 A1 | 8/2005 | Negri |
| 2005/0245839 A1 | 11/2005 | Stivoric et al. |
| 2006/0085049 A1 | 4/2006 | Cory et al. |
| 2006/0122654 A1 | 6/2006 | Bradley et al. |
| 2006/0127964 A1 | 6/2006 | Ford et al. |
| 2007/0124176 A1 | 5/2007 | Jung et al. |
| 2007/0178167 A1 | 8/2007 | Andrijauskas |
| 2009/0054742 A1 | 2/2009 | Kaminska et al. |
| 2009/0318779 A1 | 12/2009 | Tran |
| 2009/0326407 A1 | 12/2009 | Tournefier et al. |
| 2010/0081941 A1 | 4/2010 | Naghavi et al. |
| 2013/0053673 A1 | 2/2013 | Brunswick |
| 2013/0053721 A1 | 2/2013 | Brunswick |
| 2013/0204103 A1 | 8/2013 | Maarek |

OTHER PUBLICATIONS

Weber, Jessica, et al. "Novel lactate and pH biosensor for skin and sweat analysis based on single walled carbon nanotubes." Sensors and Actuators B: Chemical 117.1 (2006): 308-313.*

Hubert, D. et al.; "Abnormal electrochemical skin conductance in cystic fibrosis;" Journal of Cystic Fibrosis; Feb. 24, 2010; 6 pages.

Mayaudon, H. et al.; "A new simple method for assessing sudomotor function: Relevance in type 2 diabetes;" Diabetes & Metabolism 36 (2010); Mar. 31, 2010; pp. 450-454.

Brunswick, P. et al.; "Use of Ni electrodes chronoamperometry for improved diagnostics of diabetes and cardiac disease;" Proceedings of the 29th Annual International Conference of the IEEE EMBS, Lyon France, Aug. 23-26, 2007; pp. 4544-4547.

Khalfallah, K. et al.; "Noninvasive Galvanic Skin Sensor for Early Diagnosis of Sudomotor Dysfunction: Application to Diabetes;" IEEE Sensors Journal, vol. 12, No. 3, Mar. 2012; pp. 456-463.

Cronin, Jane; Mathematics of Cell Electrophysiology, vol. 63, 1981, p. 23.

Chizmadzhev, Yuri A., et al.; "Electrical Properties of Skin at Moderate Voltages: Contribution of Appendageal Macropores," Biophysical Journal, vol. 74, Feb. 1998, pp. 843-856.

Atkins, Peter, et al.; "Atkins' Physical Chemistry," Eighth Edition, 2006, pp. 1-1053.

Gin, H, et al.; "Non-invasive and Quantitative Assessment of Sudomotor Function for Peripheral Diabetic Neuropathy Evaluation," Diabetes Metab, 2011, doi: 10.1016/j.diabet.2011.05.003, 6 pages.

Allen, John: "Topical Review; Photoplethysmography and its application in clinical physiological measurement," IOP Publishing, vol. 28, No. 3. Mar. 1, 2007, pp. R1-R39.

Awad, Aymen A. et al.; "The Relationship Between the Photoplethysmographic Waveform and Systemic Vascular Resistance," Journal of Clinical Monitoring and Computing, vol. 21, No. 6, Oct. 17, 2007, pp. 365-372.

Li, Jin et al; "Computation of Cardiac Output by Pulse Wave Contour," IEEE, 2007, pp. 1088-1090.

Millasseau, Sandrine C. et al.; "Contour analysis of the photoplethysmographic pulse measured at the finger," Journal of Hypertension, vol. 24, No. 8, Aug. 2006, pp. 1449-1456.

Wang, L. et al.; "Noninvasive Cardiac Output Estimation Using a Novel Photoplethysmogram Index," 31st Annual International Conference of the IEEE EMBS, Minneapolis, MN, Sep. 2-6, 2009, pp. 1746-1749.

* cited by examiner

METHOD FOR PERFORMING A PHYSIOLOGICAL ANALYSIS WITH INCREASED RELIABILITY

CROSS-REFERENCE TO RELATED APPLICATIONS

This application is a National Phase Entry of International Application No. PCT/EP2012/072388, filed on Nov. 12, 2012, which claims priority to French Patent Application Serial No. 1160601, filed on Nov. 21, 2011, both of which are incorporated by reference herein.

FIELD OF THE INVENTION

The invention generally relates to the field of electrochemistry, and more particularly the field of electrophysiological analysis of the human body, for example, with views to detecting pathologies. The invention may notably be applied to the evaluation of the sudoral function of the human body.

BACKGROUND

The applicant in patent FR 2 912 893 already proposed an electrophysiological analysis system comprising a series of electrodes intended to be positioned in different regions of the body of a patient, a DC voltage source, adapted for generating adjustable DC voltage square wave pulses, and a switching circuit, laid out for selectively connecting a pair of so-called active electrodes to the voltage source, said active electrodes making up an anode and a cathode, and for connecting at least one other electrode in high impedance. The voltage applied by the voltage source on the electrodes gives the possibility of generating in the external layer of the skin, an electrophysiological current, for which the study of certain characteristics may indicate certain pathologies. Thus for example, a low slope of the voltage-current curve may be an indication, in a diabetic patient, of diabetic neuropathy, as described in document "Gin H, et al., *Non-invasive and quantitative assessment of sudomotor function for peripheral diabetic neuropathy evaluation*, Diabetes Metab (2011), doi:10.1016/j.diabet.2011.05.003W.

In order to allow proper interpretation of the measurements acquired by means of this system, the quality and the relevance of this measurement has to be ensured. Therefore, it is necessary to ensure on the one hand that the model used for relating the measurements to the actual behavior of the body is reliable and relevant. On the other hand, measurements as accurate as possible have to be conducted, by limiting at most the uncertainties and the biases related to the measurement system.

Now the voltammogram (i.e. the voltage-current curve of the response of a dipole) of an electrode, typically in nickel or stainless steel, used as an anode or cathode, was studied in solutions mimicking sweat, which is illustrated in FIG. 1. In a way known per se, oxidation and reduction reactions respectively at the anode and at the cathode are encountered, related to the application of a potential on these electrodes. On the anode side, chlorides participate in the oxidation of the anode and a wall is formed beyond a certain voltage threshold. On the cathode side, a reduction of possible oxides and reduction of the water present in the sweat are encountered, causing evolvement of hydrogen. The cathode is then reduced, which also leads to the formation of a wall below a voltage threshold.

The position of these oxidation and reduction walls on the voltammogram depends on the electrode (composition, rate of use) as well as on concentrations of electrolytes causing oxidation-reduction reactions. The voltammogram thus represents the intrinsic behavior of the electrode, i.e. the maximum current which it may transmit for a given potential, and which is governed by the charge transfer between the electrode and the electrolyte. It is understood that oxidation of the anode involves gradual generation of an overvoltage which biases the measurements. It is therefore necessary to obtain more accurate measurements than those obtained up to now with the system described hereinbefore, in particular by correcting the measurement biases related to the electrodes.

SUMMARY

One of the objects of the invention is to overcome the problems mentioned hereinbefore by proposing an electrophysiological analysis method during which the acquired measurements are more reliable and relevant than in the prior art. In particular, the object of the invention is to correct the biases which may occur during the measurement. Another object of the invention is to propose a specific model of the caused electrochemical phenomena upon applying a potential through electrodes, in order to make the interpretation of the measurements more reliable.

For this purpose, the invention proposes an electrophysiological analysis method applied in a system comprising:

a series of electrodes, intended to be placed in different regions of the human body, a DC voltage source controlled, so as to generate DC voltage square wave pulses, a switching circuit, laid out for selectively connecting a pair of so-called active electrodes to the voltage source, said active electrodes forming an anode and a cathode, and for connecting at least one other high-impedance passive electrode which is used for measuring the potential attained by the body, and a measurement circuit laid out for reading the data representative of the current in the active electrodes and of the potentials on at least certain electrodes connected as high impedances in response to the application of square waves, said data allowing determination of a value of the electrochemical conductance of the skin, the method comprising at least one measuring step during which the adjustable DC voltage source applies to the anode a series of said DC voltage square wave pulses and during which the measuring circuit reads said data, the method being characterized in that it further comprises a step before the measuring step, during which an electrode which is connected as a high impedance during the measuring step, is regenerated by connecting it to the voltage source as a cathode.

Advantageously, but optionally, the method according to the invention further comprises at least one of the following characteristics:

during the regeneration step, the cathode is subject to a continuous potential comprised between −1 and −4 V, preferably between −3 and −3.5 V, the voltage source delivers a voltage square wave pulse with a duration comprised between 5 seconds and one minute, preferably between 10 and 30 seconds, or it delivers square waves of identical or variable voltage from one square wave to the next, the cumulated duration of the square waves then being comprised in 5 seconds and one minute, preferably between 10 and 30 seconds.

during a regeneration step, the measurement circuit reads representative data of the current in the active electrodes, of their potentials, and of potentials on at least certain electrodes connected in high impedance.

The method may comprise an additional regeneration step, before the measuring step, during which another electrode connected as a high impedance during the measuring step is regenerated by being connected to the voltage source as a cathode. The method may then comprise a step for calculating the average of the potentials of the regenerated electrodes, connected as a high impedance.

The voltage square wave pulses applied during the measuring step have a duration greater than or equal to 0.2 seconds.

The DC voltage applied to the anode is less than 10V, and preferably comprised between 0V and 4V.

The voltage source delivers during the measuring step, variable voltage square wave pulses from one square wave to the other.

Each electrode is positioned on an area from the following group: right hand, left hand, right foot, left foot, right side of the forehead, left side of the forehead.

During the method, the electrochemical conductance of the skin is calculated locally at the anode and at the cathode from data respectively read at the anode and at the cathode.

The electrochemical conductance of the skin determined at the anode or at the cathode is the slope of the curve measured in a current-voltage graph for voltages applied to the anode of less than 2 V, independently of any overvoltage.

The method may further comprise an intermediate step between the regeneration step and the measuring step, during which the voltage difference between a non-regenerated electrode connected in high impedance and a regenerated electrode connected in high impedance is measured, said difference giving the possibility of determining an overvoltage value at the non-regenerated electrode, and, during the measuring step, the non-regenerated electrode for which the overvoltage has been measured is connected as an anode. The method may then comprise a step for determining from the overvoltage of the non-regenerated high impedance electrode, a correction to be applied to the measured values during the measuring step. In this case, the regenerated electrode connected as a high impedance during the intermediate step was connected beforehand as a cathode, and the method comprises a step in which the overvoltage determined during the intermediate step is subtracted from the potential measured at the anode during the measuring step.

The method comprises an additional regeneration step, between the regeneration step and the measuring step, during which the anode and the cathode are respectively the same as those of the measuring step. The conductance of the skin at the cathode is then obtained by dividing the current measured at the cathode by the potential difference between the cathode and a regenerated electrode connected as a high impedance. If required, an overvoltage is estimated at the anode by the value of the potential at the anode extrapolated to when the current becomes zero, and the conductance of the skin at the anode is obtained by dividing the current measured at the anode by the difference between the potential of the anode subtracted with said overvoltage and the potential of a regenerated electrode connected as a high impedance.

The cumulated duration of the applied voltage square wave pulses during the measuring step is comprised between 5 seconds and one minute, preferably between 10 and 30 seconds, The cumulated duration of the applied voltage square wave pulses during the measuring step being greater than or equal to the duration of the square waves applied during a regeneration step.

During the method, the overvoltage at the anode is estimated by the value of the potential at the anode extrapolated to when the current becomes zero, and the conductance of the skin at the anode is obtained by dividing the current measured at the anode by the difference between the potential of the anode subtracted with said overvoltage and the potential of a regenerated electrode connected as a high impedance.

The method comprises at least one additional regeneration step, prior to the measuring step, during which the electrode used as an anode during the measuring step is regenerated by connecting it to the voltage source as a cathode, the method may then comprise a cycle of steps for regenerating electrodes and of measuring steps, in which, for each measuring step, the anode and at least one electrode connected as a high impedance have been regenerated beforehand during at least two regeneration or measuring steps. In this case, the cathode used during a measuring step is switched as an anode during a subsequent measuring step. If the method is applied in a system comprising four electrodes, for each measuring step, the anode and both electrodes connected as a high impedance have been regenerated beforehand during regeneration or measuring steps.

During the method, a conductance of the skin at the anode is measured by dividing the current measured at the anode by the potential difference between the anode, the overvoltage having been subtracted therefrom, and a regenerated electrode connected in high impedance, and wherein the thereby obtained electrode chemical conductance of the skin corresponds to the electric conductance of the walls of the eccrine sudoriparous glands in contact with the active electrodes.

The invention also relates to a method for modeling the electric conductance of the walls of eccrine sudoriparous glands comprising the application of the method according to the invention with electrodes placed in the region of the relevant eccrine glands.

BRIEF DESCRIPTION OF THE FIGURES

Other features, objects and advantages of the current invention will become apparent upon reading the detailed description which follows, with reference to the appended figures, given as non-limiting examples and wherein.

DETAILED DESCRIPTION OF A PREFERRED EMBODIMENT

Modeling of the Electrochemical Behavior of the Skin at Low Voltages

Figure 1:
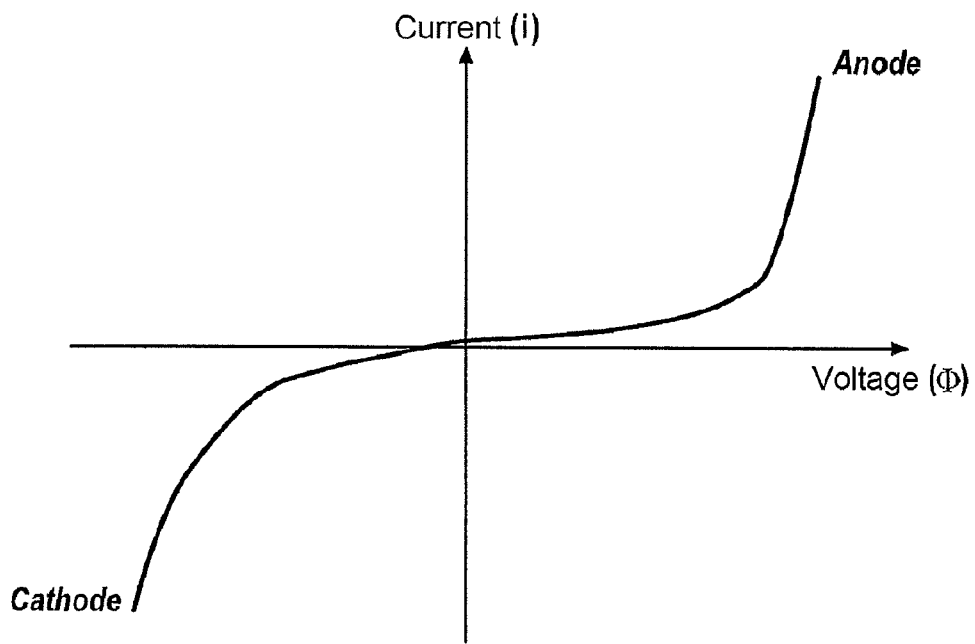
FIG. 1, already described, schematically illustrates the voltammogram of an electrode being used as an anode and as a cathode in the method according to the invention.
Figure 2:
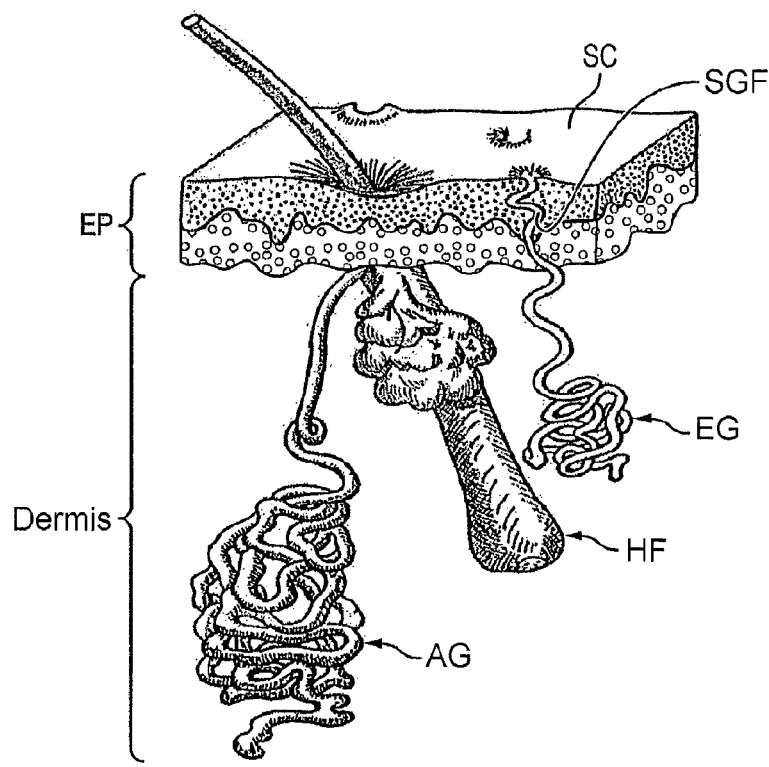
FIG. 2 is a simplified illustration of the human skin.

An improved model of the electrochemical behavior of skin subject to an electric potential was designed. The main elements of the skin considered in the model are described with reference to FIG. 2.

At the low voltages used in the method according to the invention, i.e. below 10V, the most external layer of the skin P, the stratum corneum SC, is electrically insulating. This layer, comprised in the epidermis EP, consists of a matrix of lipids and corneocytes, i.e. dead cells. It is crossed by hair follicles HF and by follicles of the sweat glands SGF, as schematized in FIG. 2. Then only the follicles of the sweat glands SGF are electrically conducting.

It is recalled that both types of sweat glands are involved in electrochemical measurements. The appocrine glands AG are localized in hairy areas such as the armpits, the pubic bone or the breast, and have a secreting channel which opens into the hairy follicle. These glands are localized in areas not concerned by the measurements and will therefore not be considered in the following.

The eccrine glands EG, as for them, are the most numerous and are quasi-present over the whole surface of the skin. They are abundantly found (on average 500/cm$^2$) on the palms of the hands, the soles of the feet and on the forehead, there where the measurements are conducted. This model particularly relates to the electrochemical behavior of the follicles of eccrine glands.

General Law of Conservation

Let us consider a continuous medium: $\rho$ is the density or specific gravity, U is the velocity, in a material volume $\Omega(t)$ having a boundary $\partial\Omega(t)$ with an external normal n, the volume (depending on time t) which we are going to study and follow in its movement. The spatial coordinate (i.e. the position) is noted as $\underline{x}\in\Omega(t)$.

Let $\alpha(\underline{x},t)$ be a sufficiently regular vector or scalar field; a resulting equation for the amount $(\rho, \alpha)$ may be written in the general form:

$$\frac{\partial}{\partial t}(\rho\ a) + div(\rho\ a \otimes \underline{U}) = \mathcal{A} + div(A)$$

wherein $\mathcal{A}$ is a production/disappearance (volume) term, A is an exchange flow (surface), $\otimes$ designates the usual vector product, and $$\frac{\partial}{\partial t}$$

is the partial time derivative.

And in the present case of a one dimensional (1D) space, one obtains:

$$\frac{\partial}{\partial t}(\rho\ a) + \frac{\partial}{\partial x}(\rho\ a\ u) = \mathcal{A} + \frac{\partial A}{\partial x}$$

The conserved standard physical quantities are: the mass, the momentum and the energy. The latter is of less interest here since it introduces additional variables including at least the temperature. For the two other ones, in the absence of viscous forces and of a pressure gradient, one has:

| Result | a | A |
|---|---|---|
| Mass | 1 | 0 |
| Momentum | $\underline{U}$ | 0 |

Wherein ($\mathcal{F}$) is the resulting force of the external bulk forces.

Model of the Gland

Figure 3:
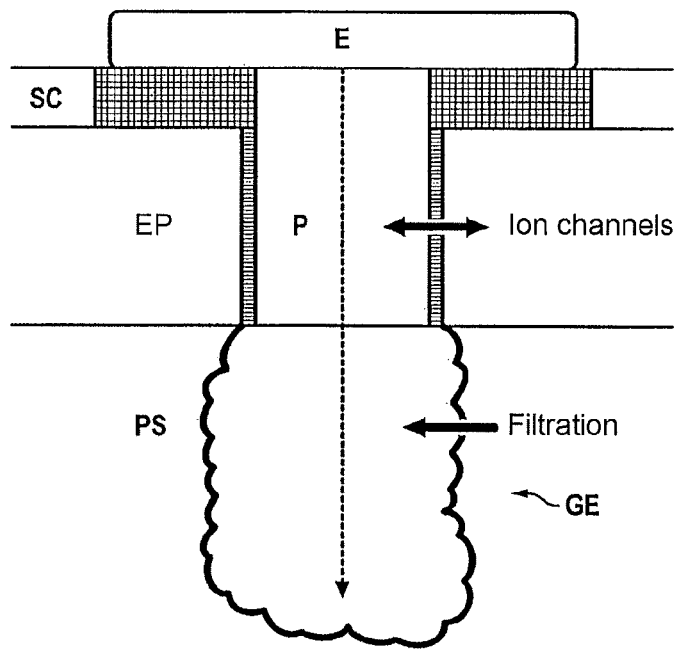
FIG. 3 schematically illustrates an eccrine sweat gland.

With reference to FIG. 3, a model of an eccrine gland EG is schematically illustrated. The eccrine gland EG consists of two portions: the secreting portion SP, where sweat is filtered (isotonically) from blood plasma, is a coil. The excreting portion EP wherein certain species may move in both directions through an ion channel (absorption or excretion, depending on their electrochemical gradient), is an almost linear conduit which leads to a pore P at the surface of the skin. Both regions have a length of the same order of magnitude, and the coil is slightly wider than the conduit.

The geometrical model consists of unrolling the coil and joining it to the conduit in order to form a cylindrical tube, like in the model of Chizmazdhev (see on the subject Y. A. Chizmadzhev, A. V. Indenbom, P. L. Kuzmin, S. V. Galichenko, J. C. Weaver, and R. O. Potts, *Electrical Properties of Skin at Moderate Voltages: Contribution of Appendageal Macropores, Biophys. J.*, vol. 74, pp. 843-856 (1998).

The main variables are the concentrations $c_i$ and velocities $u_i$ of the main ions present in sweat: $i\in\{Cl^-, Na^+, H^+\}$. We have to add the electric potential inside the gland $\Phi$. They are all dependent on (x, t), wherein x is the abscissa along the axis normal to the surface of the skin and orientated towards the inside of the body and t is the time.

The geometrical parameters are:

h: thickness of the stratum corneum (SC), $r_e$: radius of the conduit, and $r_s$: radius of the coil, $L^e$, $L^s$ respective lengths of the excreting portion and of the secreting portion.

The electric parameters are:

$\sigma$: conductivity of the electrolyte (sweat), $\Phi^A$: potential applied to the anode, $\Phi^{ext}$: constant potential attained by the body after applying an anode voltage. In the following and in order to simplify the analysis and the calculation, we shall assume $\Phi^{ext}=0$, i.e. this potential will be selected as a reference.

Surface conductances of both portions: $G^e$, $G^s$. Generally, they depend on the potential difference between both sides of the wall of the gland ($\Phi-\Phi^{ext}$).

Two currents are present: an axial current along the axis of the gland, due to the movements of the ions along the axis, and transverse currents due to the charges which cross or accumulate on the wall of the gland.

Axial Current

The surface density of the axial current, depending on the main variables, is by definition:

$$J^a = F\sum_i z_i \cdot c_i \cdot u_i$$

wherein $z_i$ is the charge of the ion i and F is the Faraday constant (charge of one mole).

The axial current is then given by:

$$I^\alpha = \pi \cdot r^2 \cdot J^\alpha$$

Moreover, Ohm's law stipulates that the current=(the conductance*the potential difference) and the conductance=(the conductivity*the surface)/the length, which gives:

$$I^a = -\sigma \cdot \pi r^2 \frac{\partial \Phi}{\partial x}$$

The electric field $\mathbb{E}$ is inferred therefrom, which by definition is:

$$\mathbb{E} \equiv -\frac{\partial \Phi}{\partial x} = \frac{F}{\sigma}\sum_i z_i \cdot c_i \cdot u_i$$

Transverse Current Through the Wall

The transverse current through the wall corresponds to the charges which cross the wall of the gland, called the ion channel current. It is related to the ions Cl⁻ and Na⁺ which pass through the epithelial membrane by using their own specific ion channels. The approach via the ion channel is a more fruitful approach than a simple conductance model since it also takes into account the chemical gradient. The current density $J_i^t$ for an ion i is given by:

$$J_i^t = z_i \cdot G_i \cdot P_i \cdot (\Phi - \Phi^{ext} - \Phi_i)$$

Wherein $G_i$ is the conductance per unit surface; $P_i$ is the percentage (or probability) of open channels, depending on the ion concentrations of each side of the wall, and generally given by a Boltzmann function; $\Phi_i$ is the potential at ion equilibrium according to Nernst's law (see on the subject: "J. Cronin, *Mathematics of Cell Electrophysiology*, New York: Marcel Dekker, Vol. 63, Lecture Notes in Pure and Applied Mathematics (1981)):

$$\Phi_i = \frac{R \cdot T}{z_i \cdot F} \cdot \ln\left(\frac{c_i}{c_i^{ext}}\right)$$

wherein R is the ideal gas constant and T is the absolute temperature.

Capacitive Transverse Current

It corresponds to the ions which accumulate on the wall of the gland. Its density (per unit surface of the wall of the gland) is written as:

$$C_w \cdot \frac{\partial \Phi}{\partial t}$$

for an electric capacity $C_w$ of the wall. However, this current is not obvious for modeling with our variables: $c_i$, $u_i$ and is transient (i.e. it disappears in stationary states). For both of these reasons, it will not be taken into account here, since the focus is mainly on permanent solutions.

Conservation of Mass

We saw that the conservation of mass is written as:

$$\frac{\partial}{\partial t}(\rho) + \frac{\partial}{\partial x}(\rho\ u) = \mathcal{A}$$

Now the source term $\mathcal{A}$ remains to be specified, which represents per unit of volume, the loss or the gain due to the transverse current through the wall.

But firstly, it is recalled that for an ion i, its density $\rho_i$ is related to its concentration $c_i$ through the simple relationship:

$$\rho_i = c_i \cdot M_i$$

wherein $M_i$ is the constant molar mass of the ion.

One finds:

$$\mathcal{A} = -\frac{2 M_i}{r \cdot F} \cdot J_i^t$$

Finally, with the concentration, the equation of conservation of mass is given by:

$$\frac{\partial c_i}{\partial t} + \frac{\partial (c_i \cdot u_i)}{\partial x} = \frac{-2}{r \cdot F} J_i^t$$

Conservation of Momentum

It was seen that the conservation of momentum is written as:

$$\frac{\partial}{\partial t}(\rho\ u) + \frac{\partial}{\partial x}(\rho\ u^2) = \mathcal{F}$$

The source term $\mathcal{F}$ now remains to be specified, which represents per unit volume, the resultant of the present external forces.

It is considered that the ions are rigid spheres moving in an incompressible continuous fluid. It is recalled that when charged species move, they generate an electric field $\mathbb{E}$ (already mentioned) and a magnetic field $\mathbb{B}$. By supposing that thermal agitation and the interactions between the species and with the wall are negligible, and that Stokes' law is applicable, the species are subject to the following forces:

The Lorentz force:

$$z_i \cdot e \cdot \mathbb{E} + z_i \cdot e \cdot u_i \wedge \mathbb{B}$$

The second term is strictly zero in our one-dimensional model since it is orthogonal to the velocity.

The drag due to the opposition of the sweat:

$$-\xi_i \cdot (u_i - v)$$

Wherein v is the constant velocity of the sweat and $\xi_i$ is the Stokes coefficient given by:

$$\xi_i = 6\pi \cdot \mu \cdot H_i$$

With μ the dynamic viscosity of the sweat (therefore of water) and $H_i$ is the hydrodynamic radius of the ion.

The resulting force is:

$$\mathcal{R}_i = z_i \cdot e \cdot \mathbb{E} - \xi_i \cdot (u_i - v)$$

And per unit volume:

$$\mathcal{F}_i = \mathcal{R}_i \cdot \frac{\rho_i}{m_i} \equiv \mathcal{R}_i \cdot \frac{c_i \cdot M_i}{m_i}$$

The law of conservation of momentum is finally inferred therefrom:

$$\frac{\partial(c_i \cdot u_i)}{\partial t} + \frac{\partial(c_i \cdot u_i^2)}{\partial x} = \frac{z_i \cdot e}{m_i} \cdot c_i \cdot \mathbb{E} - \frac{\xi_i}{m_i} \cdot c_i \cdot (u_i - v)$$

Application of a Voltage Through an Electrode

When an electrode is applied on the skin, it fills the tube so that the physiological sweat and its components are blocked: the velocity is therefore zero (v=0). Application of a potential implies that only the species which will react (Cl$^-$ at the anode and H$^+$ at the cathode) will begin to accelerate towards the electrode by electromigration. Initially and in a permanent state, the other species are at rest. As a conclusion, only Cl$^-$ and H$^+$ are concerned by this.

Simplifications: The Momentum

In the stationary state, the momentum equation is reduced to:

$$c = c^* + C \cdot \left[ \frac{\partial \Phi}{\partial x} \cdot \frac{\partial}{\partial x}\left(\frac{1}{c}\right) + \frac{2}{c} \cdot \frac{\partial^2 \Phi}{\partial x^2} \right]$$

$$c^* = \frac{\xi \cdot \sigma}{e \cdot F}$$

$$C = \frac{\sigma^2 \cdot m}{F^2 \cdot e}$$

It is recalled that the Stokes coefficient (or friction coefficient) is given by:

$$\xi = 6 \cdot \pi \cdot H \cdot \mu$$

wherein $\mu$ is the dynamic viscosity of the water, and H is the hydrodynamic radius (or Stokes radius) of a chloride ion or of a proton. This radius is in fact inferred from the mobility of the ion in the electrolyte, defined by:

$$\mathcal{M} = \frac{z \cdot e}{\xi}$$

which has been tabulated, see on this subject: P. W. Atkins and J. D. Paula, *Elements of Physical Chemistry*, Oxford University Press (2005).

In order to obtain certain orders of magnitude of the quantities c* and $\mathcal{C}$, here are certain numerical applications, first with the chloride:

| | |
|---|---|
| M (chloride Cl$^-$) | $7.91 \cdot 10^{-8}$ m$^2 \cdot$ s$^{-1} \cdot$ V$^{-1}$ |
| H (chloride Cl$^-$) | 1 Å = $10^{-10}$ m |
| $\mu$ | 0.001 kg/(m $\cdot$ s) |
| $\sigma$ | 0.01 S/cm |
| e | $1.602176 \cdot 10^{-19}$ C |
| F | 96485 C/mol |
| $m = \frac{M}{N}$ | $\frac{35 \cdot 10^{-3} \text{ kg/mol}}{6.0221415 \cdot 10^{23} \text{/mol}}$ |

Being aware that for the Coulomb unit:

$$C = A \cdot s = V \cdot S \cdot s = \frac{J}{V} = \frac{1}{V} \cdot \frac{\text{kg} \cdot \text{m}^2}{s^2} = \frac{10^4}{V} \cdot \frac{\text{kg} \cdot \text{cm}^2}{s^2}$$

One obtains:

| | | |
|---|---|---|
| c* | $1.21935 \cdot 10^{-4} \frac{\text{mol}}{\text{cm}^3} \approx 120 \frac{\text{mmol}}{\text{L}} = c^{ext}$ | |
| $\mathcal{C}$ | $3.896 \cdot 10^{-25}$ | |

If it is assumed that c=c*=constant, an $$\text{error} \approx \frac{2\mathcal{C}}{c^*} \cdot \frac{\partial^2 \Phi}{\partial x^2}$$

is committed.

As $$\frac{\partial^2 \Phi}{\partial x^2} = \frac{2G}{r \cdot G}.$$

$\Phi$ with the following orders of magnitude:

| | |
|---|---|
| G | $10^{-6}$ S/cm2 |
| r | 0.001 cm |
| $\Phi$ | 1 V |

It is found that:

Error $\approx 16 \cdot 10^{-22}$ mol/cm$^3$

Thus, it clearly appears that the second term on the right $\mathcal{C}$ is absolutely negligible, which leads to a constant distribution of the concentration along the axis, equal to that at the interstice. This simple result is remarkable and simplifies the mass equation since the potential at equilibrium $\Phi_i$ will be strictly zero.

And for the proton, $\mathcal{M} = 36.23$ then H=$2.3459 \cdot 10^{-11}$ m, which gives:

$$c^* = 28.15 \frac{\text{mmol}}{\text{L}}, \text{ pH} = 1.55$$

Thus, with the proton, there exists a discontinuity of contact at the end of the coil. Finally, the velocity is inferred from the potential $\Phi$ (see the next section), by Ohm's Law:

$$u = \mathcal{M} \cdot \frac{\partial \Phi}{\partial x}$$

With the already defined mobility (ratio of the velocity of the particle over the applied electric field):

$$\mathcal{M} = \frac{\sigma}{c^* \cdot F} = \frac{e}{\xi}$$

Simplification: The Mass

For the proton, no dedicated canal exists, this is for all purposes. Thus $P_i=1$ et $\Phi_i=0$.

For the chlorides, it has just been seen that in a permanent state, $c_i(x)=\text{const.}=c^{ext}$ which implies that the equilibrium potential (Nernst's potential) is strictly zero: $\Phi_i=0$.

In every case, in the stationary state, the conservation of mass is reduced to an ordinary differential equation for the potential:

$$\frac{d^2\Phi}{dx^2} = \frac{2}{r \cdot \sigma} \cdot P \cdot G \cdot \Phi$$

Thus, total decoupling is observed between the equations: first the conservation of mass gives the possibility of obtaining the potential, and then the conservation of momentum gives the concentration and the velocity (previous section).

In the following, it is assumed that the conductances are constant and that the dependency relatively to the potential is ensured by the probability of the opening of a channel and/or by the electroporation function $P(\Phi)$, Case of Constant Probabilities In the case of constant probabilities $P=1$, the previous ordinary differential equation of order 2, becomes an equation with constant coefficients and with the general standard solution:

$$\Phi(x) = C_1 \cdot e^{\gamma x} + C_2 \cdot e^{-\gamma x}$$

wherein $$\gamma = \sqrt{\frac{2 \cdot G}{r \cdot \sigma}}$$

and $C_1, C_2$ are constants to be determined depending on the boundary conditions which are:

Surface: application of a voltage $\Phi^A$ and continuity of the axial current between SC and the conduit:

$$\frac{\partial \Phi}{\partial x}(0) = \frac{\Phi(0) - \Phi^A}{h}$$

Connection between the excreting conduit and the secreting coil: continuity of the potential and of the current at $x=-L^e$.

Interior (end of the gland, boundary with the interstice): Neumann condition (continuity of the current which is zero) at $x=X$:

$$\frac{\partial \Phi(X)}{\partial x} = 0$$

This solution which may be built analytically is essential. It is what gives the electrochemical conductance of the skin as measured by the electrophysiological analysis system used in the present invention. Indeed, the measurement is conducted before any take-off of a physiological slope and therefore for an always constant probability.

More specifically, it is demonstrated that the measured conductance has the value:

$$\mathbb{C} \approx 2\pi \cdot r_e \cdot L_e \cdot G_e + 2\pi \cdot r_s \cdot L_s \cdot G_s$$

This simple relationship is remarkable: the measured electrochemical conductance of the skin is the sum of the "total real" conductance of the conduit and of the "total real" conductance of the coil. Further, it neither depends on the thickness of the stratum corneum h, nor on the conductivity of the sweat $\sigma$.

Taking into Account the Opening of the Ion Channel and Electroporation

The opening probability of a chloride channel is given by a Boltzmann law:

$$P = p_{min} + \frac{p_{max} - p_{min}}{1 + e^{-\frac{ZF}{RT}(\Phi - \Phi^{EXT} - \Phi_{1/2})}}$$

With:

| | |
|---|---|
| $p_{min}$ | Minimum probability: 0-0.1 |
| $p_{max}$ | Maximum probability: ≈1 |
| z | Apparent charge for Cl$^-$ ≈1 |
| $\Phi_{1/2}$ | Semi-activation potential (P = 0.5) to be adjusted. |

Figure 4A:
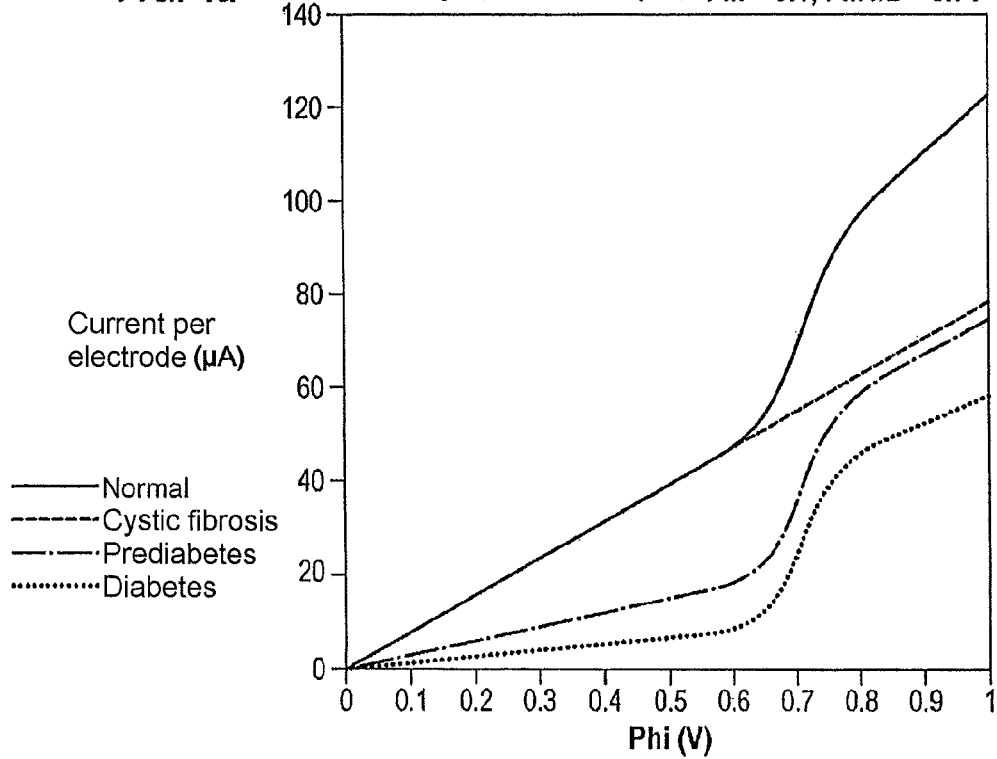
FIGS. 4a and 4b illustrate the modeling of the current-voltage response of human skin.

In FIG. 4a as an example, the Boltzmann function is illustrated for three different values of z. The Boltzmann law is combined for the opening of the channel with an electroporation model similar to the one of Chizmazdhev. In the latter, the conductance of the conduit varies exponentially with the voltage, it is a model inferred from the response of the stratum corneum to a high voltage. Electroporation is taken into account here by multiplication of the previous probability by:

$$\exp[\alpha^* \{\max(\Phi - \Phi^{ext} - \Phi_{1/2}, 0)\}^2]$$

which depends on a parameter $\alpha$ to be selected, of the order of 1. For this purpose in FIG. 4b the electroporation function for two different $\alpha$ values is illustrated.

Numerical Solution

Taking into account the opening of the channels and electroporation leads to the definition of the non-linear function $P(\Phi)$. This leads to solving the ordinary non-linear differential equation (ODE):

$$\frac{d^2\Phi}{dx^2} = \frac{2}{r \cdot \sigma} \cdot G \cdot P(\Phi) \cdot \Phi$$

Subject to the same boundary conditions as earlier (see the section "Constant Probabilities")

Therefore, this ODE should meet the same conditions on the boundaries with more than one value: one at the surface, the other one at the end of the gland. The problem which results from this is no longer the standard integration of an ODE or a problem with initial Cauchy values, but is also called a problem with boundary limits in two points.

The adopted solution is a shooting method. Integration of the ODE by the second order Stoermer algorithm proceeds from the surface up to the end of the gland, and attempts to have the boundary limit of zero current correspond with the end of the integration. The key point here is this delicate match. It is applied by using the globally convergent Newton-Raphson method.

Numerical Application

Figure 4B:
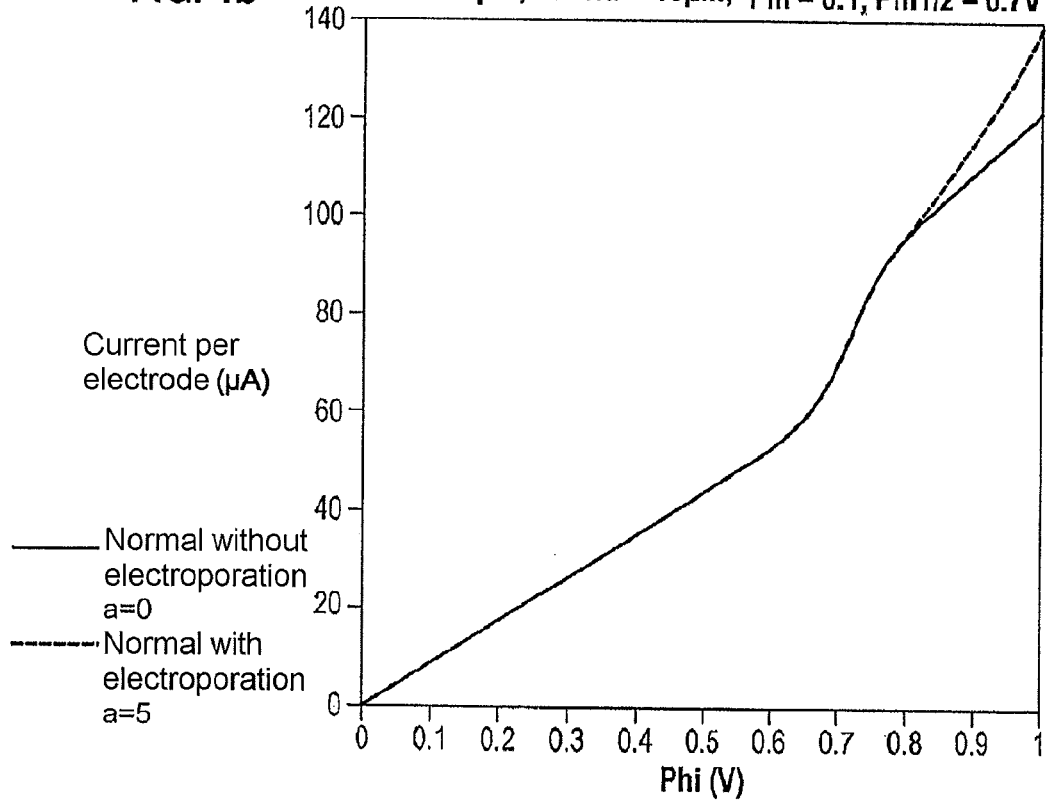

With reference to FIGS. 4a and 4b, current-voltage curves are illustrated for a gland, obtained according to the model. The main parameters which regulate the electric response of the eccrine gland are the (surface) conductances of the secreting portion and of the excreting portion. Typical values corresponding to the following cases are considered: normal patient, patient affected with cystic fibrosis, patient affected with diabetes. The orders of magnitude of the conductances are given in µS/cm².

| Conductance | Normal | Cystic fibrosis | Diabetes |
|---|---|---|---|
| Coil $G^s$ | 1-2 | 1-2 | 0.1-0.2 |
| Conduit $G^e$ | 1-2, P: 0.1-1 | 1-2 P = $P_{min}$ = 0.1 | 1-2 P: 0.1-1 |

As regards to the geometry of the gland, the excreting and secreting portions have almost the same diameter and the same length, here in cm:

| Size | Length | Radius |
|---|---|---|
| Coil | 0.1-0.5 | 0.003-0.004 |
| Conduit | 0.1-0.5 | 0.001 |

The following parameters are further considered:

| | |
|---|---|
| Gland density | 500/cm2 |
| Effective contact surface area with the electrode | 30 cm2 |
| Length of the conduit and of the coil | 0.2 cm |
| Radius of the conduit | 0.0015 cm |
| Radius of the coil | 0.0035 cm |
| Minimum probability | 0.1 |
| Sweat conductivity | 0.01 S/cm |
| Thickness of the SC | 0.004 cm |

In FIG. 4a, the modeling of the current-voltage curve is obtained for different types of patients, (healthy, diabetic, "pre-diabetic", affected with cystic fibrosis) and taking into account the probabilities of opening of the channels. In FIG. 4b, this modeling is achieved for a healthy patient, either considering electroporation or not. It is finally seen that the current-voltage characteristic in a permanent condition of the human skin initially has a linear portion before the slope takes off (or a deviates from linearity) which stems from the non-linear dependence of surface conductance of the gland/tube relatively to the voltage due to the opening of the channels and/or to electroporation.

Electrophysiological Analysis Method

Figure 5:
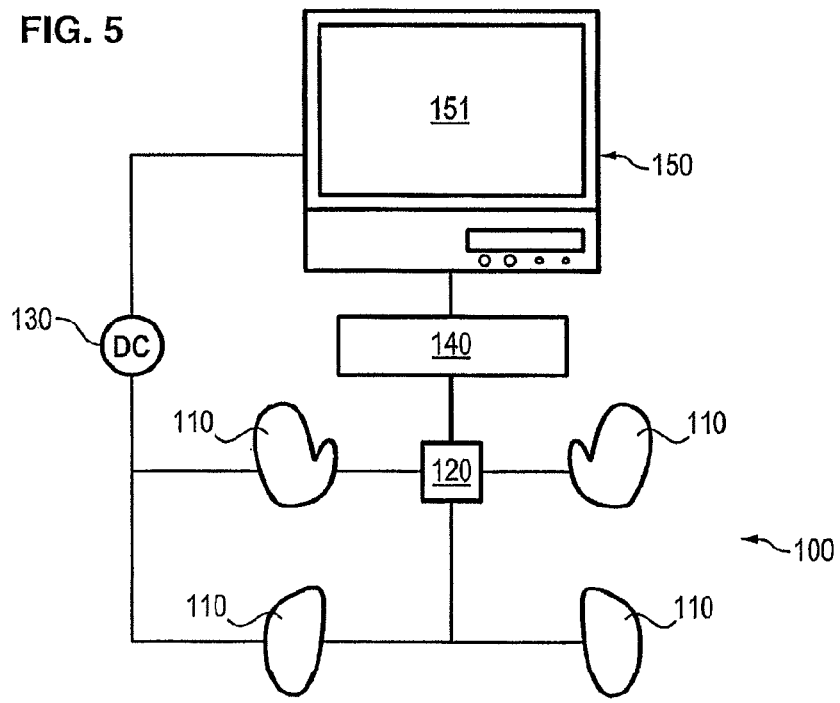
FIG. 5 represents an analysis system used in the method according to the invention.

The model discussed hereinbefore indicates that the measurement of the conductance of the skin gives the possibility of strictly determining the conductance of the walls of the eccrine glands, i.e. the capability of the gland of secreting ions. Thus, when a potential is applied on these glands, the sweating function is exactly evaluated which is impacted in certain diseases such as diabetes or cystic fibrosis. This result is used in the method according to the invention, in which the electrochemical conductance of skin is measured. To do this, an electrophysiological analysis system 100 schematized in FIG. 5 is provided.

This system 100 comprises a plurality of electrodes 110, at least two electrodes of which for the feet (left food, right foot), two electrodes of which for the hands (left hand, right hand), and two electrodes for the forehead (left portion of forehead, right portion of the forehead). Alternatively, it only comprises four electrodes 110, for the hands and feet.

Typically with a four electrode system as described above, the measurements are conducted with the following pairs of electrodes (abbreviated designation between brackets):

| Anode | Cathode |
|---|---|
| Left hand (MG) | Right hand (MD) |
| Right hand (MD) | Left hand (MG) |
| Left foot (PG) | Right foot (PD) |
| Right foot (PD) | Left foot (PG) |

These electrodes are preferably of large dimensions, i.e. their surface is comprised between 50 and 200 cm², so that they cover the whole surface of the analyzed area. These electrodes, once they are applied onto the skin, are subject to a potential allowing electrochemical phenomena, studied in the model hereinbefore, to be established.

In order to be able to be measured by an electrode, the current due to the transport of sweat ions of in the gland should be less than the current which may be transmitted by the electrode and which is due to the transfer of electrons between the electrode and the sweat. This condition is here ensured by the use of sensitive electrodes consisting of materials such as nickel or stainless steel, which allow phenomena to be viewed even at low voltages (<10 V). In order to apply a potential to the skin, these electrodes are connected to an adjustable DC voltage source 130, adapted for delivering DC voltage square wave pulses.

The system also comprises a switching circuit 120. This circuit may selectively connect one or several electrodes as a high impedance and connect a pair of other ones to the voltage source. The latter are so-called active electrodes, since they apply the potential on the skin in order to conduct the measurements.

The system further comprises a measurement circuit 140, which measures representative data of the current and of the potential in the active electrodes and potentials on at least one electrode connected in high impedance. This measurement circuit may also comprise or be connected to a processor 150, suitable for treating the data, and if required display them as a curve on a display 151. The measurement is successively and independently made on the hands and on the feet by alternating left and right. At each time, two electrodes are active: the anode with the imposed positive potential $V^\alpha$ and the cathode with a measured potential $V^C$, the current between them is also measured.

Further, at least one other passive high impedance electrode is connected to the ground. Preferably, this is the case of both passive electrodes noted as XG and XD (X=hand or foot, D=right, G=left) with measured potentials $V^{XG}$ and $V^{XD}$ allowing the potential attained by the body to be recovered $V^X \approx V^{XG} \approx V^{XD}$. Thus, the electrochemical conductance of the skin is traditionally measured at the anode and at the cathode, by dividing the current between the electrodes by the respective potential at the anode and the cathode, from which the potential of the high impedance electrode and optionally an electrode correction are subtracted. In the case where a plurality of electrodes is connected in high impedance, the average potential is calculated for determining the electrochemical conductance of the skin at the anode and at the cathode.

During the measurement step, the voltage source delivers to the anode one or more voltage square wave pulses, with a duration greater than or equal to 0.2 seconds. Preferably the cumulated duration of the whole of the square wave pulses is comprised between 5 seconds and one minute, and preferably comprised between 10 and 30 seconds. This duration is sufficiently long for allowing electrochemical phenomena to be established in the skin.

The square waves have a potential comprised in 1 and 4 V. The voltage source may apply to the anode several square waves of equal duration and of variable voltage from one square wave to the other, for example increasing or decreasing between 1 and 4 V. Alternatively, it may simply apply a single square wave with a voltage comprised between 1 and 4 V, preferably between 3 and 3.5 V.

Figure 6:
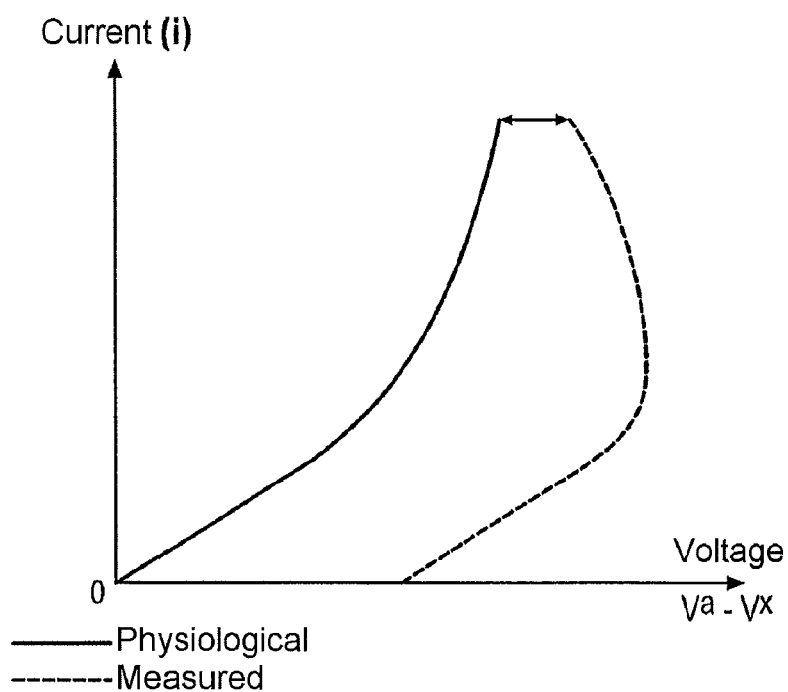
FIG. 6 illustrates the measurement bias between the physiological current and the actually measured current at the anode.

As described in the preamble, the oxidation of the anode generates at the latter an overvoltage which increasingly changes over time and depending on the potential applied to the anode. On the other hand, at the cathode, the reduction causes a decrease in the overvoltage until the latter is cancelled out. These overvoltages have the effect of distorting the measurement, as visible in FIG. 6.

In this figure, the curve in solid lines represents the physiological current to be measured, which should normally pass through the origin. The curve in dotted lines represents the actually measured current, depending on the difference between the potential at the anode and the potential of the body, the latter being measured by electrodes and connected as a high impedance.

The method according to the invention allows correction of this measurement. For this purpose, the principle of regenerating the electrodes consisting of connecting an electrode and a cathode for suppressing any overvoltage, is used. To do this, the method according to the invention has at least one additional step prior to the measuring step, during which at least one electrode is regenerated, by using it as a cathode, before connecting it as a high impedance electrode.

During such a regeneration step, the cathode is subject to a DC potential comprised between −1 and −4 V, and preferably between −3 and −3.5 V. This potential results from applying to the anode a DC voltage in the form of a single square wave pulse, or of several square waves of variable voltages or not from one square wave pulse to the other. Preferably, the total duration of the voltage application is greater than the time for regenerating the cathode, comprised between a few seconds a few tens of seconds. For example, it may be comprised between 5 seconds and one minute, or preferably between 10 and 30 seconds.

The fact that a high impedance electrode is regenerated gives the possibility of guaranteeing that the potential measured at this electrode exactly corresponds to a potential attained by the body at this area. This guarantees that the potential difference between the active electrodes and the regenerated electrode allows exact determination of the potential, and therefore of the electrochemical conductance of the skin at the active electrodes.

The method may further comprise an additional regeneration step for one or several other electrodes which are connected as a high impedance during the measuring step. In this case, the average of their potentials is calculated for obtaining the potential attained by the body. Of course, it is possible to use a regeneration step also as a measuring step. In this case, the measuring circuit measures the potentials at the electrodes connected as a high impedance, the potential at the cathode, and the current between the anode and the cathode. Finally, the method may utilize the methods explained hereafter for suppressing the biases in the measuring step.

Method of the Performing Cycle

This method consists of performing a cycle of successive steps of regeneration and of measurements utilizing the fact that an electrode used as a cathode in either type of step (measurement or regeneration step) is regenerated.

The cycle therefore comprises:
  at least one step for regenerating a high impedance electrode during which said electrode, connected as a high impedance in the measuring step, is connected as a cathode,
  one step for regenerating an anode, during which the anode of the measuring step is connected as a cathode,
  and a measuring step.

Many cycles may be devised. It is possible to envision a cycle during which the cathode used during a measuring step is used as an anode during a subsequent measuring step. Alternatively, a cycle is generated during which the electrochemical conduction of the skin on hands and on feet are measured from the potential of the anode (conductance related to the chloride ions); therefore at least four measurements have to be conducted wherein the anode is located on four different sites: right hand, left hand, right foot, left foot.

A possible cycle in which both electrodes connected as a high impedance and the anode are always regenerated, is the following:

| Anode-Cathode | Nature of the step | Comments |
|---|---|---|
| MG-PG | Regeneration | PG regenerated subsequently |
| MG-PD | Regeneration | PD regenerated subsequently |
| MG-MD | Regeneration | MD regenerated subsequently |
| MD-MG | Measurement | Anode regeneration at the beginning, MG regenerated subsequently |
| MG-MD | Measurement | Anode regeneration at the beginning, MD regenerated subsequently |
| PG-MG | Regeneration | MG regenerated subsequently |
| PD-PG | Measurement | Anode regenerated at the beginning, PG regenerated subsequently |
| PG-PD | Measurement | Anode regenerated at the beginning |

During this cycle, the anodes are always regenerated, and the "zero" is ensured for both electrodes connected as a high impedance; the result of this is that the left and right measurement circuits are symmetrical. Of course, the scope of the method is not limited to this cycle, or to the use of only four electrodes. Its principle may easily be transposed to other cycles or to a larger number of electrodes, for example six electrodes.

Method for Measuring the Conductance with the Slope of the Curve

Returning to FIG. 6, it is seen that the linear conductance of the physiological current is the slope of the straight portion of the measured current. Therefore, it is possible to calculate the linear conductance of the physiological current by determining the slope of the curve while low voltages are applied to the anode, once the over voltage on the anode and cathode sides is stabilized. Another method for utilizing the slope of the curve consists of estimating the overvoltage at the anode by extrapolating the potential when the current becomes zero, and then determining the conductance (either linear or not) of the skin at the anode by dividing the current by the difference between the potential of the anode from which this overvoltage has been subtracted, and the potential of a regenerated electrode connected as a high impedance.

Measurement of the Conductance with Electrode Correction

In addition to the preceding determination of the overvoltage from the slope, the conductance may also be estimated with an electrode correction.

Alternatively, the method according to the invention may comprise an intermediate step, during which an overvoltage is estimated with a potential difference between a regenerated electrode connected in high impedance, and another non-regenerated electrode, connected in high impedance. During this measurement, the DC voltage source always delivers to the anode one or several voltage square wave pulses with the same voltage and duration as described earlier. The thereby measured potential difference allows determination of the overvoltage when this non-regenerated electrode will be used as an anode during a subsequent measurement step.

An estimation of the electrochemical conductance of the skin is obtained at the anode by dividing the current between the anode and the cathode by the difference between the corrected potential of the anode (from which the overvoltage is subtracted) and the potential of the regenerated electrode connected in high impedance.

Duplication Method of the Measurement

Alternatively, the method according to the invention comprises an additional regeneration step, comprised between the regeneration step and the measuring step, during which the anode and the cathode are respectively the same as in the measuring step. During this step, the cathode is completely regenerated, while the overvoltage at the anode increases in order to attain the final offset.

Figure 7:
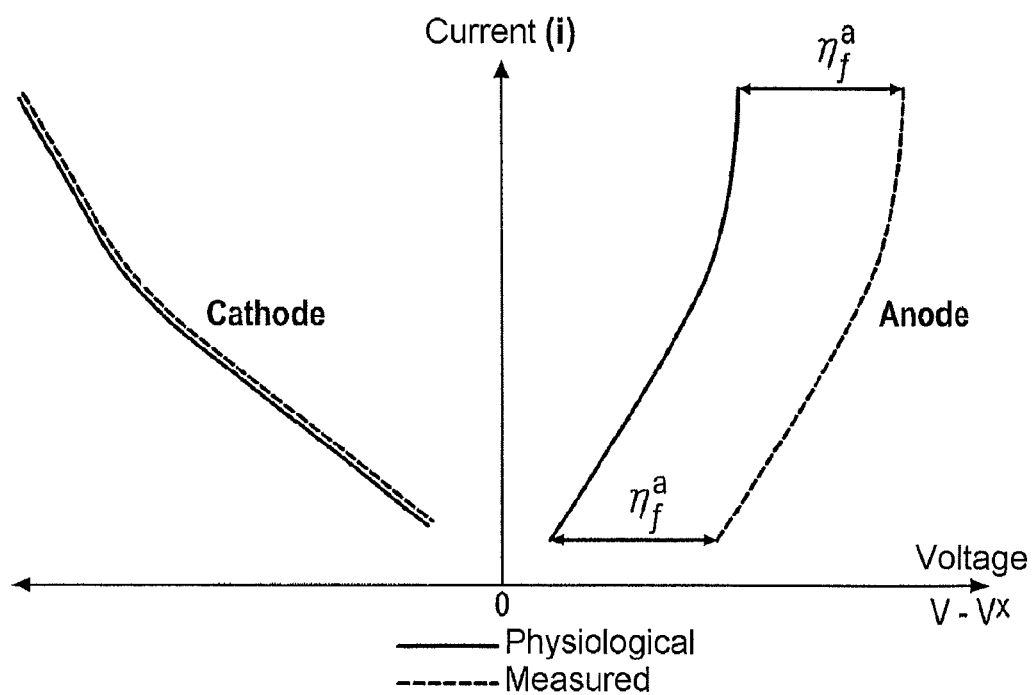
FIG. 7 illustrates an example of current-voltage curves measured at the anode and at the cathode according to an alternative of the method.

Therefore, as visible in FIG. 7, during the subsequent measurement step, the curve measured on the cathode side, in dotted lines, coincides with the physiological current in solid lines. On the other hand, at the anode, the overvoltage is constant and equal to the final offset $\eta_f^\alpha$ i.e. the measured current in dotted lines and the physiological current in solid lines are simply shifted by the offset. This allows an accurate evaluation of the whole curve at the anode and at the cathode: both the linear conductance portion and the taking-off portion.

Indeed, in the voltage ranges for which the conductance of the skin is linear, this conductance may be estimated at the anode, like at the cathode by measuring the slope of the current-voltage curve. Moreover, it is also possible to determine the conductance of the skin at the taking-off portion, at the anode like at the cathode.

At the cathode, it is sufficient to divide the current between the electrodes by the potential at the cathode, from which the potential of a regenerated high impedance electrode has been subtracted. At the anode, the current between the electrodes is divided by the potential difference between the anode and a regenerated high impedance electrode, from which the voltage at the anode has been subtracted. By means of the invention, one skilled in the art will be able to apply accurate measurement methods for the electrochemical conduction to the skin and may infer therefrom the presence in a patient of dysfunctions and pathologies, such as for example cystic fibrosis or autonomic neuropathy.

The invention claimed is:

1. An electrophysiological analysis method applied in a system comprising:
    a series of electrodes including active and passive electrodes configured to be placed in different regions of a human body,
    a DC voltage source, controlled for increasing DC voltage square wave pulses,
    a switching circuit selectively connecting a pair of the active electrodes to the voltage source, the active electrodes forming an anode and a cathode, and the switching circuit connecting at least one of the passive electrodes with impedance being used for measuring potential attained by the body, and
    a measuring circuit measuring representative data of current in the active electrodes and potentials on at least certain electrodes connected with impedance in response to the application of the square waves, the data allowing determination of a value of electrochemical conductance of skin, the method further comprising:
    at least one measuring step during which the adjustable voltage source applies to the anode a series of the DC voltage square waves, and during which the measuring circuit measures the data,
    a step prior to the measuring step, during which an electrode which is connected with impedance during the measuring step is regenerated by being connected to the voltage source as a cathode; and
    an intermediate step, between the regeneration step and the measuring step, during which a voltage difference is measured between a non-regenerated electrode connected with impedance and a regenerated electrode connected with impedance, the difference allowing determination of an overvoltage value at the non-regenerated electrode, and wherein, during the measuring step, the non-regenerated electrode, the overvoltage of which has been measured, is connected as an anode.

2. The electrophysiological analysis method according to claim 1, wherein, during the regeneration step, the cathode is subject to a DC potential comprised between −1 and −4V.

3. The electrophysiological analysis method according to claim 1, wherein, during the regeneration step, the voltage source delivers a voltage square wave pulse with a duration comprised between 5 seconds and one minute.

4. The electrophysiological analysis method according to claim 1, wherein, during the regeneration step, the voltage source delivers square wave pulses with an identical or variable voltage from one pulse to the other.

5. The electrophysiological analysis method according to claim 4, wherein the cumulative duration of the square wave pulses is comprised between 5 seconds and one minute.

6. The electrophysiological analysis method according to claim 1, wherein, during a regeneration step, the measuring circuit measures the representative data of the current in the active electrodes, of their potentials, and of the potentials on at least certain electrodes connected in impedance.

7. The electrophysiological analysis method according to claim 1, comprising an additional regeneration step prior to the measuring step, during which another electrode connected with impedance during the measuring step is regenerated while being connected to the voltage source as a cathode.

8. The electrophysiological analysis method according to claim 7, comprising a step for calculating the average of the potentials of the regenerated electrodes connected with impedance.

9. The electrophysiological analysis method according to claim 1, wherein the applied voltage square wave pulses during the measuring step have a duration of greater than or equal to 0.2 seconds.

10. The electrophysiological analysis method according to claim 1, wherein the DC voltage applied to the anode is less than 10 V.

11. The electrophysiological analysis method according to claim 1, wherein the voltage source during the measuring step delivers square wave pulses with variable voltages from one pulse to the other.

12. The electrophysiological analysis method according to claim 1, wherein each electrode is positioned on an area from among the following group: the right hand, left hand, right foot, left foot, right side of the forehead, left side of the forehead.

13. The electrophysiological analysis method according to claim 1, wherein the electrochemical conductance of the skin at the anode and at the cathode is calculated by a processor from data respectively measured at the anode and at the cathode, and showing a curve on a display connected to the processor.

14. The electrophysiological analysis method according to claim 1, comprising a step for determining from the overvoltage of the non-regenerated high impedance electrode, a correction to be applied to the values measured during the measuring step.

15. The electrophysiological analysis method according to claim 14, wherein the regenerated electrode connected with impedance during the intermediate step was connected beforehand as a cathode, and comprising a step in which the overvoltage determined during the intermediate step is subtracted from the potential measured at the anode during the measuring step.

16. The electrophysiological analysis method according to claim 1, comprising an additional regeneration step, between the regeneration step and the measuring step, during which the anode and the cathode are respectively the same as those of the measuring step.

17. The electrophysiological analysis method according to claim 1, wherein the cumulative duration of the square wave voltage pulses applied during the measuring step is comprised between 10 and 30 seconds.

18. The electrophysiological analysis method according to claim 17, wherein the cumulative duration of the square wave voltage pulses applied during the measuring step is greater than or equal to the duration of the applied square wave during a regeneration step.

19. The electrophysiological analysis method according to claim 18, wherein an overvoltage at the anode is estimated by the value of the potential at the anode extrapolated to when the current becomes zero, and the conductance of the skin at the anode is obtained by dividing the current measured at the anode by the difference between the potential of the anodes subtracted with the overvoltage and the potential of a regenerated electrode connected with impedance.

20. The electrophysiological analysis method according to claim 18, wherein the square wave pulses applied during the measuring step are of increasing or decreasing voltage from one pulse to the other, and the conductance of the skin at the anode is determined by measuring the slope of the current-voltage curve are measured at the anode for voltages of less than 2 V.

21. The electrophysiological analysis method according to claim 1, comprising at least one additional regeneration step, prior to the measuring step, during which the electrode used as an anode during the measuring step is a regenerated by being connected to the voltage source as a cathode.

22. The electrophysiological analysis method according to claim 21, comprising a cycle of electrode regeneration steps and of measuring steps, wherein, for each measuring step, the anode and at least one electrode connected with impedance were regenerated during at least two regeneration or measuring steps.

23. The electrophysiological analysis method according to claim 22, wherein the cathode used during a measuring step is switched to as an anode during a subsequent measuring step.

24. The electrophysiological analysis method according to claim 23, system comprises four electrodes, and wherein for each measuring step, the anode and the two electrodes connected with impedance were regenerated during the regeneration or the measuring steps.

25. An electrophysiological analysis method for use in a system comprising:
a series of electrodes configured to be placed in different regions of a human body,
a DC voltage source controlled for increasing DC voltage square wave pulses,
a switching circuit selectively connecting a pair of active electrodes to the voltage source, the active electrodes forming an anode and a cathode, and the switch circuit connecting at least one of the passive electrode with impedance being used for measuring potential attained by the body, and
a measuring circuit measuring representative data of current in the active electrodes and potentials on at least certain electrodes connected with impedance in response to the application of the square waves, the data allowing determination of a value of the electrochemical conductance of skin,
the method further comprising:
at least one measuring step during which the adjustable voltage source applies to the anode a series of the DC voltage square waves, and during which the measuring circuit measures the data,
a step prior to the measuring step, during which an electrode which is connected with impedance during the measuring step is regenerated by being connected to the voltage source as a cathode; and
measuring a conductance of the skin at the anode by dividing the current measured at the anode by the potential difference between the anode, the overvoltage having been subtracted therefrom, and a regenerated electrode connected with impedance, and wherein the thereby obtained electrochemical conductance of the skin corresponds to electric conductance of walls of eccrine sweat glands in contact with the active electrodes.

26. A method for modeling the electric conductance of walls of eccrine sweat glands, comprising applying the method according to claim 1 with the electrodes positioned in the region of the relevant eccrine glands.

* * * * *